United States Patent
Brown et al.

(10) Patent No.: US 9,421,238 B2
(45) Date of Patent: Aug. 23, 2016

(54) TREATMENT OF KLEBSIELLA PNEUMONIAE WITH LIPOSOMALLY FORMULATED GLUTATHIONE

(71) Applicants: Emory University, Atlanta, GA (US); YOUR ENERGY SYSTEMS, LLC, Palo Alto, CA (US); Children's Healthcare of Atlanta, Inc., Atlanta, GA (US)

(72) Inventors: Lou Ann Brown, Atlanta, GA (US); Frederick Timothy Guilford, Palo Alto, CA (US)

(73) Assignees: YOUR ENERGY SYSTEMS, LLC, Palo Alto, CA (US); EMORY UNIVERSITY, Atlanta, GA (US); CHILDREN'S HALTHCARE OF ATLANTA, INC., Atlanta, GA (US)

( * ) Notice: Subject to any disclaimer, the term of this patent is extended or adjusted under 35 U.S.C. 154(b) by 0 days.

(21) Appl. No.: 14/767,985

(22) PCT Filed: Feb. 14, 2014

(86) PCT No.: PCT/US2014/016495
§ 371 (c)(1),
(2) Date: Aug. 14, 2015

(87) PCT Pub. No.: WO2014/127245
PCT Pub. Date: Aug. 21, 2014

(65) Prior Publication Data
US 2015/0366933 A1    Dec. 24, 2015

Related U.S. Application Data

(60) Provisional application No. 61/765,379, filed on Feb. 15, 2013.

(51) Int. Cl.
*A61K 9/127* (2006.01)
*A61K 38/06* (2006.01)
*A61K 9/00* (2006.01)
*A61K 9/48* (2006.01)

(52) U.S. Cl.
CPC .............. *A61K 38/063* (2013.01); *A61K 9/127* (2013.01); *A61K 9/006* (2013.01); *A61K 9/0014* (2013.01); *A61K 9/0019* (2013.01); *A61K 9/0095* (2013.01); *A61K 9/4858* (2013.01)

(58) Field of Classification Search
CPC .................................................... A61K 9/127
See application file for complete search history.

(56) References Cited

U.S. PATENT DOCUMENTS

| 5,569,464 | A  | * | 10/1996 | Endo ..................... | A61K 9/127 424/450 |
| 5,843,473 | A  | * | 12/1998 | Woodle ................. | C07F 9/5537 424/450 |
| 2006/0099244 | A1 | * | 5/2006 | Guilford ............... | A61K 9/127 424/450 |
| 2010/0069309 | A1 | * | 3/2010 | Gage .................... | A61K 38/063 514/1.1 |

OTHER PUBLICATIONS

Burns et al. (1998). "Microbiology of Sputum from Patients at Cystic Fibrosis Centers in the United States." Clinical Infectious Diseases, 27: 158-163.*
Schairer Do et al, "Evaluation of the Antibiotic Properties of Glutathione," J Drugs Dermatology, Nov. 1, 2013, vol. 12, No. 11, pp. 1272-1277 PMID 24196336.
Mehta et al, "Alcoholism causes alveolar macrophage zinc deficiency and immune dysfunction," Am J Respir Crit Care Med. Sep. 15, 2013, vol. 188, No. 6,pp. 716-723. PMID 23805351.
Klebsiella pneumoniae in Healthcare Settings(published by Centers for Disease Control) http://www.cdc.gov/HAI/organisms/klebsiella/klebsiella.html downloaded Apr. 27, 2016.
Block, W, PEGylaated Liposomes Increase Bioavailability, Molecular stalth technology rolongs release and minimizes toxicity and side effects (citation below) Life Enhancement (magazine), http://www.life-enhancement.com/magazine/article/1106-pegylated-liposomes-increase-bioavailability (published by Life Enhancement Products, Inc., Aug. 2005 downloaded Apr. 15, 2016).
Zeevalk et al, Characterization of intracellular elevation of glutathione (GSH) with glutathione monethyl ester and GSH in brain and neuronal cultures: Relevance to Parkinson's disease, 203 Experimental Neurology 512-20 (2007). PMCID: PMC1839874.
Allen et al, Effects of Oral Glutathione Supplementation on Systemic Oxidative Stress Biomarkers in Human Volunteers, The Journal of Alternative and Complementary Medicine vol. 17, No. 9, 2011, pp. 827-833 (Mary Ann Liebert, Inc. Dept. 2011) PMC3162377.

* cited by examiner

*Primary Examiner* — Gollamudi S. Kishore
*Assistant Examiner* — Amanda Heyes
(74) *Attorney, Agent, or Firm* — Brooke Schumm, III; Daneker, McIntire, Schumm, Prince, Manning & Widmann, P.C.

(57) ABSTRACT

The composition of the invention, liposomal glutathione, has been recently shown to have utility for having an antibiotic like effect on *Klebsiella pneumonia* cultures in vitro, and in vivo as demonstrated by efficacy in reducing by large multiples the presence of cultures of *Klebsiella* in rats in animal tests. Further, because the liposomal glutathione bolsters body defenses as well as appearing to have direct killing action, the propensity to create more and more resistant strains to antibiotic treatment is downgraded.

4 Claims, No Drawings

TREATMENT OF KLEBSIELLA PNEUMONIAE WITH LIPOSOMALLY FORMULATED GLUTATHIONE

TECHNICAL FIELD

Statement of Industrial Applicability

The invention relates to the use of liposomally formulated reduced glutathione to treat *Klebsiella*.

BACKGROUND

*Klebsiella pneumonia* is a growing issue in intensive care units as it is a common bacterial contaminant that has become relatively refractory to current treatment regimes. Additionally, because *Klebsiella* tends to be omnipresent in the body, though well controlled, the intensive care unit functions as an incubator for strains of *Klebsiella* that have shown an increasing pattern of producing ever more antibiotic resistant strains of *Klebsiella pneumoniae* in patients.

SUMMARY OF INVENTION

Technical Problem

The technical problem is finding and enabling a composition to diminish the growth of *Klebsiella pneumonia* cultures in the patient's body, particularly in lung tissue. Further, the technical problem is to use a composition that interrupts the cycle of incubation of ever more resistant strains of *Klebsiella* in patients surviving *Klebsiella* infection.

Solution to Problem

Based on a research at Emory University, and enabled in humans by the co-inventor, the inventors propose administration of liposomally formulated reduced glutathione ("liposomal glutathione" or "liposomal reduced glutathione") according to the specifications below for treatment of *Klebsiella pneumonia*, and pneumonia more generally. The enablements herein would improve response to any form of pneumonia, but will be directed to *P. klebsiella*, and can be applied by a person skilled in the art in the same way to pneumonia more generally.

Advantageous Effects of Invention

The composition of the invention, liposomal glutathione, has been recently shown to have utility for having an antibiotic like effect on *Klebsiella pneumonia* cultures in vitro, and in vivo as demonstrated by efficacy in reducing by large multiples the presence of cultures of *Klebsiella* in rats in animal tests. Further, because the liposomal glutathione bolsters body defenses as well as appearing to have direct killing action, the propensity arising from surviving *Klebsiella* bacteria to create more and more resistant strains to antibiotic treatment is downgraded.

DESCRIPTION OF EMBODIMENTS

The purpose of the present application is to reference the use of liposomally encapsulated reduced glutathione as method of treating *Klebsiella* and as a means of preventing and reversing the formation of cultures of *Klebsiella*. Research has shown that the use of N-Acetyl Cysteine (NAC), a building block of glutathione can have the effect of reversing the oxidative stress in cells. A lack of adequate glutathione in the defensive immune cells such as macrophages can lead to serious deficits in immune defense against infection as related in the discussion of Venketaraman and Brown studies below. However as explained below, NAC requires the function of the enzymes needed to combine the three amino acids of glutathione as well as energy to formulate intracellular glutathione, which energy is often not available in a cell. A compromise of energy and enzyme function occurs because of oxidative stress induced by infections such as *Klebsiella*. Cysteine, as found in NAC has been the only possible oral method, however inefficient, to increase glutathione though it is not particularly effective and no showing has been made of in vivo application. Non-formulated glutathione itself, as a tripeptide, does not survive passage of the gut to be physiologically effective to individual cells such as in lung tissue. Liposomally encapsulated reduced glutathione, the present invention, has been shown in an unpublished study (Lauver) to raise glutathione levels in tissues after oral ingestion in a rabbit model of ischemia (low oxygen) followed by the return of blood flow and oxygen (i.e., reperfusion) injury. Research was commissioned at the University of Michigan, as yet unpublished, showing the surprising effect of the invention in reversing and controlling oxidative stress in tissues such as that which occurs in individuals with illnesses severe enough to require Intensive Care Unit (ICU) admission (PMID 8989180); individuals in the ICU have been shown to be deficient in glutathione due to compromise of the enzymes responsible for the production of glutathione. No publications reference the use of liposomal reduced glutathione to raise tissue levels of glutathione as documented in Lauver et al, University of Michigan Medical School, "Oral Pretreatment With Liposomal Glutathione Attenuates Reperfusion Injury in Rabbit Isolated Hearts," to be published in the Journal of Cardiovascular Pharmacology (2013), That study shows that contrary to the usual degradation in the gut, the invention, purchased from Your Energy Systems, LLC of Palo Alto, Calif., in the amount of approximately 428.8 mg of GSH administered in 5 ml doses, had the following abstracted result:

"A liposomal preparation of glutathione (lipGSH) capable of oral administration was investigated for its ability to attenuate tissue injury and increase myocardial glutathione levels in an isolated heart model of reperfusion injury. Male, New Zealand white rabbits were assigned randomly among four groups: control and daily oral administration of lipGSH for three, seven or fourteen days. At completion of the dosing regimen, hearts were harvested and perfused in a retrograde manner with the use of a Langendorff apparatus. The hearts were subjected to 30 min of global ischemia followed by 60 min of reperfusion. Hearts from lipGSH-treated rabbits exhibited better recovery of left ventricular contractile function during reperfusion and had attenuated oxidative damage. Furthermore, hearts from lipGSH-treated animals had increased myocardial tissue levels of GSH demonstrating effective absorption of lipGSH."

The invention proposes that based on the Lauver et al unpublished research, the administration of liposomally encapsulated glutathione pursuant to the invention would raise the level of intracellular glutathione by at least 30%, particularly in tissues oxidatively stressed.

Plain, non-formulated glutathione used orally is not an option for this therapy as plain glutathione is not absorbed after oral ingestion in humans (1). A rat study of the removal of a radio-tagged metal (CO-60) from the liver, performed at Pacific Northwest National Laboratory with oral liposomally encapsulated reduced glutathione confirms this observation. The animals receiving:
a. Control (water only) showed 100% of the toxin remained=0% removal
b. Plain glutathione, oral, in water showed 100% of the toxin remained=0% removal.
c. Intravenous glutathione showed 36% of the toxin remaining=64% removal.
d. Liposomal reduced glutathione showed 53% of the toxin remaining=47% removal.

The data from this study is consistent with the observation that liposomally encapsulated glutathione is almost as effective as intravenous glutathione in removing the toxin. The plain glutathione has little if any absorption or efficacy. Levitskaia et al, Aminothiol Receptors for Decorporation of Intravenously Administered $^{60}$Co In The Rat, Health Physics, Vol. 98(1) No. 4: 53-60 (Health Physics Society 2009).

Oral liposomally encapsulated reduced glutathione that is uniquely designed to be absorbed a) across the mucosa of the nose, mouth, gastrointestinal tract, b) after topical application for transdermal, or c) by intravenous infusion of glutathione with or without liposome encapsulation is prepared under the method and according to the composition described as follows:

Basic Dosing Information

For a typical adult ranging from 55 kg to 90 kg, the dose of oral liposomally encapsulated reduced glutathione is oral liposomally encapsulated reduced glutathione 422 mg (1 teaspoon) (5 ml each) at least twice a day. More preferable is administration of 4 teaspoons (5 ml each) 4 times per day. If the initial does is tolerated well, a loading dose of another 1-5 teaspoons (5 ml-25 ml) after perhaps an hour would be helpful.

(2) The concentration of the glutathione in the liposomes can be in a range from 3.3% w/w to 9% w/w or higher.

Deionized water can be used to bring w/w percentages up to 100% w/w in any of the tables or formulations below.

Dosing

Selenium should also be administered 200 mg per day if there is inadequate selenium in a patient.

Liposomally encapsulated reduced glutathione (also referred to as liposomal glutathione or liposomal reduced glutathione or liposome-encapsulated glutathione): The preferred dosing schedule of the invention for the treatment of symptoms related to treatment of Klebsiella is 800 mg (2 teaspoons) of the invention to be taken twice a day on an empty stomach (that is: do not ingest until 30 minutes after eating solid food) and may administered orally or through a nasogastric tube.

1 teaspoon of the invention of oral liposomally encapsulated reduced glutathione contains approximately 420 mg reduced glutathione ("GSH"), and may contain 423 mg reduced glutathione, and 428 mg reduced glutathione.

A preferred mode sets a suggested dose based on body weight. Recommended amounts are for use in the treatment of Klebsiella. For best results it is suggested that the invention be used if there is a finding of Klebsiella. Gently stir liposomally encapsulated reduced glutathione into the liquid of your choice.

Determine Individual Dose by Body Weight: For Children
Under 30 lbs: ¼-½ teaspoon=100-200 mg GSH
30-60 lbs: ½-1 teaspoon=210-420 mg GSH
60-90 lbs: ¾-1.5 teaspoon=316 mg-630 GSH
90-120 lbs: 1-2 teaspoon=422-844 mg GSH
120-150 lbs: 1½-3 teaspoon=630-1260 mg GSH
Over 150 lbs: 1½-3 teaspoons=630-1260 mg GSH The invention should be used on a continuous basis.

Children—should use a dose of liposomally encapsulated reduced glutathione equivalent to 60 mg/Kg of body weight daily in divided doses.

These doses should be continued for the duration of the duration of the illness and for purposes of maintaining adequate glutathione in tissues before, during and after therapy for Klebsiella.

DETAILED DESCRIPTION OF THE PREFERRED EMBODIMENTS

The methods of manufacture described in Keller et al U.S. Pat. No. 5,891,465, U.S. Pat. No. 6,610,322, and U.S. Pat. No. 6,726,924 and U.S. provisional application No. 60/597,041 by this inventor are adopted herein and into the modes of this invention and can be applied to the examples without undue experimentation. Liposomal formulations preferred in this invention can be purchased from Biozone, Inc. of Pittsburgh, Calif. Reduced glutathione can be b purchased from Sigma-Aldrich of St. Louis, Mo. or from Kyowa Hakko USA, Inc., 767 3$^{rd}$ Ave. No. 9, of New York City, N.Y. 10017 with a Western regional office at 85 Enterprise, Suite 430, Aliso Viejo, Calif. 92656. Liposomally encapsulated reduced glutathione can be purchased from Your Energy Systems, LLC, 555 Bryant St., Suite 305, Palo Alto, Calif. 94301.

Example 1

Liposomal Glutathione Drink or Spray 2500 mg Per Ounce or Form Suitable for Encapsulation or Gel

|  | % w/w |
|---|---|
| Deionized Water | 74.4 |
| Glycerin | 15.00 |
| Lecithin | 1.50 |
| Potassium Sorbate (optional spoilage retardant) | 0.10 |
| Glutathione (reduced) | 8.25 |

A lipid mixture having components lecithin, and glycerin were commingled in a large volume flask and set aside for compounding. Hydroxylated lecithin is the preferred ingredient.

In a separate beaker, a water mixture having water, glycerin, glutathione were mixed and heated to, but not more than, 50.degree. C.

The water mixture was added to the lipid mixture while vigorously mixing with a high speed, high shear homogenizing mixer at 750-1500 rpm for 30 minutes.

The homogenizer was stopped and the solution was placed on a magnetic stirring plate, covered with parafilm and mixed with a magnetic stir bar until cooled to room temperature. Normally, a spoilage retardant such as potassium sorbate or BHT would be added. The solution would be placed in appropriate dispenser for ingestion as a liquid or administration as a spray.

Analysis of the preparation under an optical light microscope with polarized light at 400× magnification confirmed presence of both multilamellar lipid vesicles (MLV) and unilamellar lipid vesicles.

The preferred embodiment includes the variations of the amount of glutathione to create less concentrated amounts of liposomally encapsulated glutathione. The amount of glutathione added to the formulation may range from 3.3% w/w to 8.5% w/w or higher. The methods of manufacture described in Keller et al U.S. Pat. No. 5,891,465, U.S. Pat. No. 6,958,160 and U.S. Pat. No. 7,150,883 and U.S. provisional application No. 60/597,041 are incorporated in this description. Concentrations of liposomally encapsulated glutathione from 3.3% w/w, 4% w/w, 5% w/w, 6% w/w, 7% w/w, 7.5% w/w, 8% w/w, 8.5% w/w or 9% w/w liposomally encapsulated glutathione may be formed and utilized for dosing by decreasing the amounts of glutathione and preplacing the material with an increase in the sterile water concentration.

Example 1A

Liposomally encapsulated reduced glutathione Drink or Spray 2500 mg Per Ounce or Form Suitable for Encapsulation or Gel: In %, according to w/w: Deionized Water 75, Glycerin 15.00, Lecithin 1.50, Extract Potassium Sorbate 0.10, Glutathione 8.5 (reduced) A lipid mixture having components lecithin, ethyl alcohol and glycerin were commingled in a large volume flask and set aside for compounding. Hydroxylated lecithin is the preferred ingredient.

In a separate beaker, a water mixture having water, glycerin, glutathione were mixed and heated, but not more than, 50.degree C.

The water mixture was added to the lipid mixture while vigorously mixing with a high speed, high shear homogenizing mixer at 750-1500 rpm for 30 minutes.

The homogenizer was stopped and the solution was placed on a magnetic stirring plate, covered with parafilm and mixed with a magnetic stir bar until cooled to room temperature.

A spoilage retardant such as potassium sorbate or BHT would be added. The solution would be placed in appropriate dispenser for ingestion as a liquid or administration as a spray.

Analysis of the preparation under an optical light microscope with polarized light at 400× magnification confirmed presence of both multilamellar lipid vesicles (MLV) and unilamellar lipid vesicles.

The preferred embodiment includes the variations of the amount of glutathione to create less concentrated amounts of liposomally encapsulated glutathione. The amount of glutathione added to the formulation may range from 3.3% w/w to 8.5% w/w or higher. The methods of manufacture described in Keller et al U.S. Pat. No. 5,891,465, U.S. Pat. No. 6,958,160 and U.S. Pat. No. 7,150,883 and U.S. provisional application No. 60/597,041 are incorporated in this description.

Concentrations of liposomally encapsulated glutathione from 3.3% w/w, 4% w/w, 5% w/w, 6% w/w, 7% w/w, 7.5% w/w, 8% w/w, 8.5% w/w or 9% w/w liposomally encapsulated glutathione may be formed and utilized for dosing by decreasing the amounts of glutathione and preplacing the material with an increase in the sterile water concentration.

Example 2

Embodiment two of the invention includes the incorporation of the fluid liposome (such as that prepared in Example 1A) into a gelatin based capsule to improve the stability, provide a convenient dosage form, and assist in sustained release characteristics of the liposome. The present embodiment relates to the use of glutathione in the reduced state encapsulated into liposomes or formulated as a preliposome formulation and then put into a capsule. The capsule can be a soft gel capsule capable of tolerating a certain amount of water, a two-piece capsule capable of tolerating a certain amount of water or a two-piece capsule where the liposomes are preformed then dehydrated.

The liposome-capsule unit containing biologically encapsulated material can be taken in addition to orally, used for topical unit-of-use application, or other routes of application such as intra-ocular, intranasal, rectal, or vaginal.

The composition of examples 1 and 2 may be utilized in the encapsulated embodiment of this invention.

Gelatin capsules have a lower tolerance to water on their interior and exterior. The usual water tolerance for a soft gel capsule is 10% w/w on the interior. The concentration of water in a liposome formulation can range from 60-90% water. An essential component of the present invention is the formulation of a liposome with a relatively small amount of water, in the range of 5-10% w/w. By making the liposome in a low aqueous system, the liposome is able to encapsulate the biologically active material and the exposure of water to the inside lining of the capsule is limited. The concentration of water should not exceed that of the tolerance of the capsule for which it is intended. The preferred capsule for this invention is one that can tolerate water in the 15-20% w/w range.

The methods described by Keller et al, U.S. Pat. No. 6,726,924 are incorporated in this description.

Components are commingled and liposomes are made using the injection method (Lasic, D., Liposomes, Elsevier, 88-90, 1993). When liposome mixture cooled down 0.7 ml was drawn into a 1 ml insulin syringe and injected into the open-end of a soft gelatin capsule then sealed with tweezers. Filling of gel caps on a large scale is best with the rotary die method or others such as the Norton capsule machine.

Example 3

Embodiment number four of the present invention includes the creation of liposome suspension using a self-forming, thermodynamically stable liposomes formed upon the adding of a diacylglycerol-PEG lipid to an aqueous solution when the lipid has appropriate packing parameters and the adding occurs above the melting temperature of the lipid. The method described by Keller et al, U.S. Pat. No. 6,610,322 is incorporated into this description.

Most, if not all, known liposome suspensions are not thermodynamically stable. Instead, the liposomes in known suspensions are kinetically trapped into higher energy states by the energy used in their formation. Energy may be provided as heat, sonication, extrusion, or homogenization. Since every high-energy state tries to lower its free energy, known liposome formulations experience problems with aggregation, fusion, sedimentation and leakage of liposome associated material. A thermodynamically stable liposome formulation which could avoid some of these problems is therefore desirable.

The present embodiment prefers liposome suspensions which are thermodynamically stable at the temperature of formation. The formulation of such suspensions is achieved by employing a composition of lipids having several fundamental properties. First, the lipid composition must have packing parameters which allow the formation of liposomes. Second, as part of the head group, the lipid should include polyethyleneglycol (PEG) or any polymer of similar properties which sterically stabilizes the liposomes in suspension. Third, the lipid must have a melting temperature which allows it to be in liquid form when mixed with an aqueous solution.

By employing lipid compositions having the desired fundamental properties, little or no energy need be added when mixing the lipid and an aqueous solution to form liposomes. When mixed with water, the lipid molecules disperse and self assemble as the system settles into its natural low free energy state. Depending on the lipids used, the lowest free energy state may include small unilamellar vesicle (SUV) liposomes, multilamellar vesicle (MLV) liposomes, or a combination of SUVs and MLVs.

In one aspect, the invention includes a method of preparing liposomes. The method comprises providing an aqueous solution; providing a lipid solution, where the solution has a packing parameter measurement of $P_a$ ($P_a$, references the surface packing parameter) between about 0.84 and 0.88, a $P_v$ ($P_v$ references the volume packing parameter) between about 0.88 and 0.93, (See, D. D. Lasic, Liposomes, From Physics to Applications, Elsevier, p. 51 1993), and where at least one lipid in the solution includes a polyethyleneglycol (PEG) chain; and combining the lipid solution and the aqueous solution. The PEG chain preferably has a molecular weight between about 300 Daltons and 5000 Daltons. Kinetic energy, such as shaking or vortexing, may be provided to the lipid solution and the aqueous solution. The lipid solution may comprise a single lipid. The lipid may comprise dioleolylglycerol-PEG-12, either alone or as one of the lipids in a mixture. The method may further comprise providing an active compound, in this case glutathione (reduced); and combining the active compound with the lipid solution and the aqueous solution.

The low molecular weight in the preferred embodiments more effectively deliver the liposomally encapsulated reduced glutathione in active reduced form as needed and thus result in the surprising effect of the invention. The absorption into cells is a particular advantage of the preferred embodiment of the invention.

Further Examples 4

Formulation for Topical Application of Liposomally Encapsulated Reduced Glutathione A topical cream or lotion containing reduced glutathione in a self-forming liposome sold under the brand name "QuSome"® by Biozone Laboratories, Inc. of Pittsburgh, Calif. is another preferred embodiment. The Qusome self-forming liposome can be formed containing reduced liposomally encapsulated glutathione in a concentration of 5% reduced glutathione encapsulated in the liposome. Most liposomes use energy provided as heat, sonication, extrusion, or homogenization for their formation, which gives them a high energy state. Some liposome formulations can experience problems with aggregation, fusion, sedimentation and leakage of liposome associated material which this invention seeks to minimize and does minimize. The Qusome is a more thermodynamically stable liposome formulation. The Qusome self-forming liposome is self-forming at room temperature which that the mixing of the lipid and an aqueous lipid containing solution avoids alteration of the contents by heating. The resulting liposome is in a low free energy state so it remains stable and reproducible. The formulation of this embodiment is reviewed in example 3. The methods of manufacture described in Keller et al U.S. Pat. No. 6,958,160 and U.S. Pat. No. 7,150,883 are incorporated in this description. The most important details of that manufacturing are as follows:

The lipids used to form the lipid vesicles and liposomes in the present formulations can be naturally occurring lipids, synthetically made lipids or lipids that are semisynthetic. Any of the art known lipid or lipid like substances can be used to generate the compositions of the present invention. These include, but are not limited to, lecithin, ceramides, phosphatidylethanolamine, phosphotidylcholine, phosphatidylserine, cardiolipin and the like. Such lipid components for the preparation of lipid vesicles are well known in the art, for example see U.S. Pat. No. 4,485,954, and "Liposome Technology", 2nd Ed, Vol. I (1993) G. Gregoriadis ed., CRC Press, Boca Raton, Fla.

Lipids with these properties that are particularly preferred in the present formulations include phospholipids, particularly highly purified, unhydrogenated lecithin containing high concentrations of phosphotidylcholine, such as that available under the trade name Phospholipon 90 from American Lecithin, or Nattermann Phospholipid, 33 Turner Road, Danbury, Conn. 06813-1908.

In formulating the liposomes, in one aspect, the invention includes a method of preparing liposomes. The method comprises providing an aqueous solution; providing a lipid solution, where the solution has a $P_a$ between about 0.84 and 0.88, a $P_v$ between about 0.88 and 0.93, and where at least one lipid in the solution includes a polyethyleneglycol (PEG) chain; and combining the lipid solution and the aqueous solution. The PEG chain preferably has a molecular weight between about 300 Daltons and 5000 Daltons. Kinetic energy, such as shaking or vortexing, may be provided to the lipid solution and the aqueous solution. The lipid solution may comprise a single lipid. The lipid may comprise dioleolyglycerol-PEG-12, either alone or as one of the lipids in a mixture. The method may further comprise providing an active compound; and combining the active compound with the lipid solution and the aqueous solution.

In another aspect, the invention includes a liposome suspension. The suspension comprises one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain. The PEG chain preferably has a molecular weight between about 300 Daltons and 5000 Daltons. The suspension may comprise a single lipid. The lipid may comprise dioleolylglycerol-PEG-12.

The suspension may further comprise an active compound, which may be selected from the group described above.

In another aspect, the invention includes a composition for combining with an aqueous solution to form a liposome suspension. The composition comprises one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain. The PEG chain preferably has a molecular weight between about 300 Daltons and 5000 Daltons. The composition may comprise a single lipid. The composition may comprise dioleolylglycerol-PEG 12. The composition may further comprise an active compound selected from the group above. The composition may be provided in a sealed container, where the container also contains an inert gas to prevent oxidative degradation.

In another aspect, the invention includes a method of intravenously administering a therapeutic compound. The method comprises providing a composition including one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain; providing an active compound; providing an aqueous solution; combining the composition, compound and solution to form a liposome suspension; and administering the liposome suspension intravenously. The method may further comprise providing kinetic energy to the liposome suspension. The method may also include providing the composition in a sealed container containing an inert gas. The PEG chain preferably has a molecular weight between about 300 Daltons and 5000 Daltons. The composition may comprise a single lipid. The lipid may comprise dioleolylglycerol-PEG-12. The active compound may be selected from the group above.

In another aspect, the invention includes a method of solubilizing an active compound. The method comprises providing a composition including one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain; providing the active compound; providing an aqueous solution; and combining the active compound, the lipid and the aqueous solution to form a liposome suspension. The method may further comprise providing kinetic energy to the liposome suspension. The method may include providing the composition in a sealed container containing an inert gas. The PEG chain preferably has a molecular weight between about 300 Daltons and 5000 Daltons. The composition may comprise a single lipid. The lipid may comprise dioleolylglycerol-PEG-12. The active compound may be selected from the group above.

In another aspect, the invention includes a method of orally administering a therapeutic compound. The method comprises providing a composition including one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain; providing an active compound; providing an aqueous solution; combining the composition, compound and solution to form a liposome suspension; and administering the liposome suspension orally in the form selected from the group comprising a two piece hard gelatin capsule, a soft gelatin capsule, or drops.

The compositions may be administered topically, interorally, vaginally or rectally.

PEG-12 Glyceryl Dioleate was obtained from Global 7 (New Jersey) for the following formulations. This can be substituted for the lecithin w/w % as needed to accomplish the formulation, or applied as set forth below.

In the following formulations, the "set percentage" w/w % of reduced glutathione is selected from 3.3%, 4%, 5%, 6%, 7%, 7.5%, 8%, 8.5% or 9% or amounts approximately to those percentages.

Example 5A

Spontaneous Liposomes for Intravenously Administering Therapeutic Compounds or for a Spray or Drink A set percentage of reduced glutathione is dissolved in a sufficient amount of the solvent PEG-12 Glyceryl Dioleate, also called dioleolylglycerol-PEG 12, (either referred to as "PEGDO") and gently mixed for about 5 minutes. A sufficient amount of PEGDO should be about 10% w/w. Deionized water is slowly added to the solution. Ingredients other than deionized water, the reduced glutathione and the PEGDO may be added such as preferably 0.1% w/w potassium sorbate and then the final amount of deionized water added is that amount which is necessary to have the percentages add up to 100% w/w. Taste or other flavor-masking ingredients could also be added before the deionized water is brought up to 100% w/w. Although taste ingredients can be added before or after the liposomal encapsulation formulation, the preferable mode is to add flavor or other taste masking ingredients after liposomal encapsulation formulation, and they may be ingredients such as corn syrup, honey, sorbitol, sugar, saccharin, stevia, aspartame, citrus seed extract, natural peppermint oil, menthol, synthetic strawberry flavor, orange flavor, chocolate, or vanilla flavoring in concentrations from about 0.01 to 10% w/w. The inventor has preferably used citrus seed extract.

Example 5B

Spontaneous Liposomes for Intravenously Administered Therapeutic Compound and as a Drug Solubilization Vehicle for Use in Spray or Drink A set percentage of reduced glutathione is mixed with a sufficient amount of PEG-12 Glyceryl Dioleate, also called dioleolylglycerol-PEG 12, (either referred to as "PEGDO") to bring the reduced glutathione into solution by vortexing and sonication for 10 minutes. A sufficient amount of PEGDO should be about 5% w/w. Deionized water is added and gently mixed. Ingredients other than deionized water, the reduced glutathione and the PEGDO may be added such as preferably 0.1% w/w potassium sorbate and then the final amount of deionized water added is that amount which is necessary to have the percentages add up to 100% w/w. Ingredients other than deionized water, the reduced glutathione and the PEGDO may be added such as preferably 0.1% w/w potassium sorbate and then the final amount of deionized water added is that amount which is necessary to have the percentages add up to 100% w/w. Taste ingredients or other flavor masking ingredients could also be added before the deionized water is brought up to 100% w/w. Although taste ingredients can be added before or after the liposomal formulation, the preferable mode is to add flavor or other taste masking ingredients after liposomal formulation, and they may be ingredients such as corn syrup, honey, sorbitol, sugar, saccharin, stevia, aspartame, citrus seed extract, natural peppermint oil, menthol, synthetic strawberry flavor, orange flavor, chocolate, or vanilla flavoring in concentrations from about 0.01 to 10% w/w. The inventor has preferably used citrus seed extract.

The QuSome self-forming liposome uses polyethyleneglycol (PEG) is a steric stabilizer and the resulting liposome is of a moderate size, 150 nm-250 nm. The combination of 150 nm-250 nm size and the PEG component is known to create long circulating liposomes. The size of the QuSome self-forming liposome allows them to be sterile filtered.

The concentration of liposomally encapsulated glutathione in the liposomes resulting from the Qusome formulation is 5% w/w for topical application. It is possible to use the Qusome technology in creating an oral formulation also and the 8.25% glutathione in w/w concentration encapsulated in the liposome may be used in the oral formulation.

Further Examples

Example 6

The invention is a method of treatment of *Klebsiella pneumonia*, including direct action against the organism, and a composition for the treatment of *Klebsiella pneumoniae* (referenced as "*Klebsiella*" for short) by the direct action of liposomal reduced glutathione. Liposomal reduced glutathione, particularly that formulated by and sold by Your Energy Systems, LLC of Palo Alto, Calif., would be administered to mammalian patients exhibiting respiratory distress or symptoms or upon receipt of a culture identifying the presence of *Klebsiella*, particularly humans. The preferred dosage for a 70 kg patient would be 4 teaspoons daily in an oral formulation having approximately an 8.25% w/w concentration of reduced glutathione in the liposomal formulation. It could be any concentration above 3.3% w/w within the liposomes normally in increments of 0.5% w/w between 3.3% w/w and 9% w/w or higher. There are approximately 423 mg. of reduced glutathione per teaspoon but maybe 420 or 428 mg per teaspoon. Administration may be oral, by inhalation, mucosal, rectal, or intravenous administration.

The invention is directed to correcting reduced glutathione deficiencies in lung tissue(s). By increasing the concentration of reduced glutathione intracellularly in affected lung tissues, direct killing action of the *Klebsiella* organism occurs as reflected in the experiment recited below.

*Klebsiella pneumoniae* were grown overnight in Tryptic Soy Broth (99 ml of broth and 1 ml of bacteria). The broth containing the *K. pneumoniae* was divided into equal volumes, centrifuged, and the pellets were washed twice with phosphate buffered saline (PBS). After the final wash, the two pellets were resuspended, pooled, and brought to a final volume of 10 ml. The final concentration of *K. pneumonia* was ~2×1010 colony forming units per ml. After diluting this stock to 2×103 and 2×102 colony forming units per ml, 100 μl of these two dilutions were plated onto 100 mm MacConkey Agar Plates. The plates were then misted with 250 μl of liposomal glutathione (182 μl in 100 ml of PBS; Your Energy Systems, LLC, Palo Alto, Calif.) or PBS. After the plates were incubated upside down overnight at 37° C., the number of colony forming units was determined. For the plates misted with PBS, the colony forming units were 200 and 20 for the 2×103 and 2×102 dilutions, respectively. For the plates misted with liposomal glutathione, the colony forming units were 5 and 1 for the 2×103 and 2×102 dilutions, respectively.

Using a standard protocol [Yeligar et al., J. Immunol. 188 (8):3648-57 (2012)], control and ethanol-fed male C57BL/6J mice (aged 8-10 weeks; Jackson Laboratory, Bar Harbor, Me.) were given an intra-tracheal inoculation of *K. pneumoniae* (2×106 colony forming units; 100 μl). At the four hour time point, mice were randomized to treatment with an oral dose of PBS (20 μl) or liposomal glutathione (20 μl of 84.5 mg/ml). At the 20 hour time point, the colony forming units in the lung were determined. For the control mice, the colony forming units of *K. pneumoniae* in the lung fluid were 40±3 and 21±4 in the PBS and liposomal glutathione treated groups, respectively. For the ethanol-fed mice, the colony forming units of *K. pneumoniae* were 62±8 and 16±5 in the PBS and liposomal treated groups, respectively. In some studies, mice were randomized to an intranasal treatment of 25 μl per nasal nare of PBS or liposomal glutathione (182 μl in 100 ml of PBS) at the four hour time point. For the control mice, the colony forming units of *K. pneumoniae* in the lung fluid were 42±5 and 19±6 in the PBS and liposomal glutathione treated groups, respectively. For the ethanol-fed mice, the colony forming units of *K. pneumoniae* were 74±9 and 14±6 in the PBS and liposomal treated groups, respectively.

Thus an aspect of the invention is a method of treatment of *Klebsiella pneumoniae* with liposomally formulated reduced glutathione in a mammalian patient according to the dosages given above.

Another aspect of the invention is a composition of liposomally formulated glutathione formulated as set forth herein for treatment of *Klebsiella pneumoniae* in a mammalian patient according to the dosages given above.

The invention claimed is:

1. A method of treating a *Klebsiella pneumoniae* infection in a mammalian patient comprising:

orally administering liposomally formulated reduced glutathione, said liposomally formulated reduced glutathione being formulated from at least one phospholipid selected from the group of phosphatidylethanolamine or phosphatidylserine, wherein the reduced glutathione included inside the liposome is in an amount of at least 3.3% w/w.

2. A method of treating a *Klebsiella pneumoniae* infection in a mammalian patient comprising:

orally administering liposomally formulated reduced glutathione, said liposomally formulated reduced glutathione being formulated from lecithin, wherein the reduced glutathione included inside the liposome is in an amount of at least 3.3% w/w.

3. A method of treating a *Klebsiella pneumoniae* infection in a mammalian patient comprising:

orally administering liposomally formulated reduced glutathione, said liposomally formulated reduced glutathione being formulated from at least one ceramide, wherein the reduced glutathione included inside the liposome is in an amount of at least 3.3% w/w.

4. A method of treating a *Klebsiella pneumoniae* infection in a mammalian patient comprising:

orally administering liposomally formulated reduced glutathione, said liposomally formulated reduced glutathione being formulated from at least one cardiolipin, wherein the reduced glutathione included inside the liposome is in an amount of at least 3.3% w/w.

* * * * *